Figure 1:
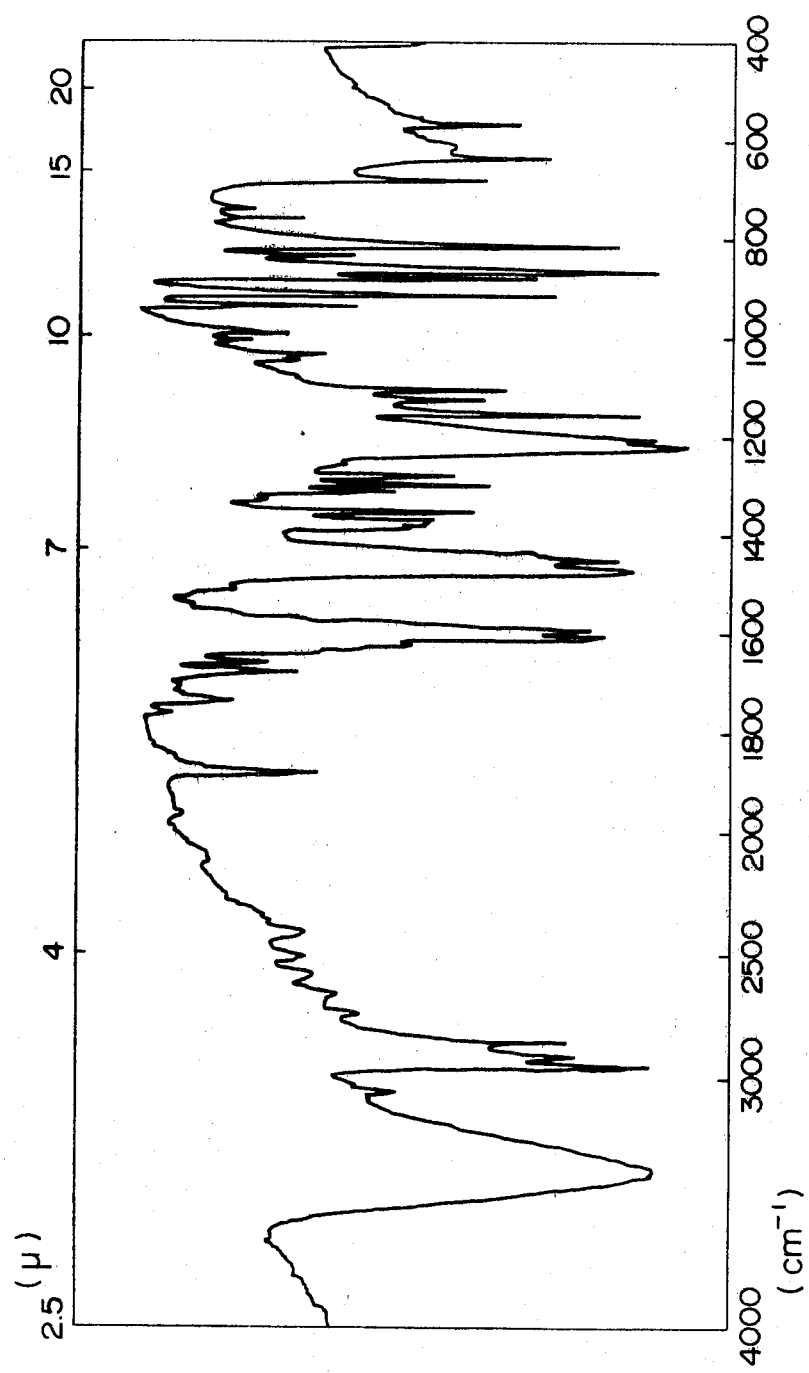

United States Patent

Numata et al.

[11] 4,366,328
[45] Dec. 28, 1982

[54] INDENE COMPOUND AND NOVEL PROCESS FOR PRODUCING INDENE COMPOUNDS

[75] Inventors: Satoshi Numata, Yokohama; Kiyoshi Nakatani, Tokyo; Noboru Yamazaki; Teruo Yuasa, both of Nagoya, all of Japan

[73] Assignee: Mitsui Toatsu Chemicals, Inc., Tokyo, Japan

[21] Appl. No.: 97,147

[22] Filed: Nov. 26, 1979

[51] Int. Cl.³ ............................................. C07C 37/52
[52] U.S. Cl. ................................................ 568/734
[58] Field of Search ............... 568/716, 734, 806, 797

[56] References Cited

U.S. PATENT DOCUMENTS

| | | | |
|---|---|---|---|
| 1,754,052 | 4/1930 | Rosenthal | 568/734 |
| 2,969,343 | 1/1961 | Morris | 568/734 |
| 3,281,478 | 10/1966 | Farnham | 568/716 |
| 3,904,617 | 9/1975 | Pelz et al. | 568/734 |
| 4,045,499 | 8/1977 | Klein et al. | 568/734 |

OTHER PUBLICATIONS

Mimaki et al., Chem. Abst., vol. 83, #96727e, (1975).
Verkhonskaya et al., Chem. Abst., vol. 83, #88316q, (1971).
Corson et al., J. Org. Chem., vol. 23, pp. 544–549, (1958).

*Primary Examiner*—James H. Reamer
*Attorney, Agent, or Firm*—Fisher, Christen & Sabol

[57] ABSTRACT

Indene compounds of the formula

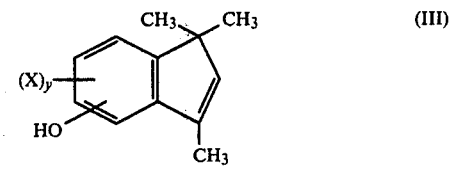

wherein
X represents a hydrogen atom, a halogen atom, a hydroxyl group or a methyl group, and
y is 0 or an integer of 1 to 3,
are produced by either heat-decomposing indene compounds of the formula

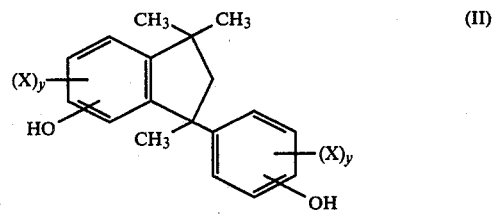

wherein
X and y are as defined, in the presence of an acid or alkaline catalyst; or heat-decomposing isopropenyl phenols of the formula

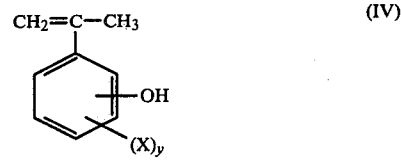

wherein
X and y are as defined,
or oligomers or polymers thereof in the presence of an acid catalyst. 5-Hydroxy-1,1,3-trimethyl-2-indene corresponding to formula (III) is a novel compound.

12 Claims, 1 Drawing Figure

INDENE COMPOUND AND NOVEL PROCESS FOR PRODUCING INDENE COMPOUNDS

This invention relates to a novel indene compound, and a novel process for producing indene compounds.

More specifically, this invention pertains to (1) a novel indene compound, 5-hydroxy-1,1,3-trimethyl-2-indene, of the formula

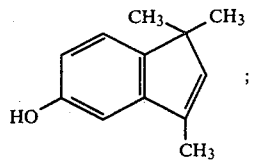

(2) a process for producing indene compounds of the formula

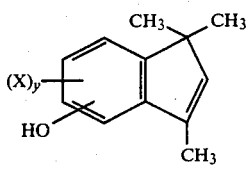

wherein

X represents a hydrogen atom, a halogen atom, a hydroxyl group or a methyl group, and y is 0 or an integer of 1 to 3, which comprises heat-decomposing indane compounds of the formula

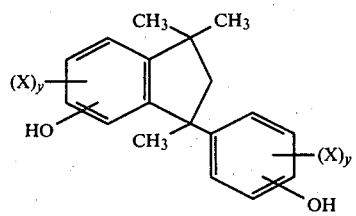

wherein X and y are as defined, in the presence of an acid or alkaline catalyst; and (3) a process for producing indene compounds of the formula

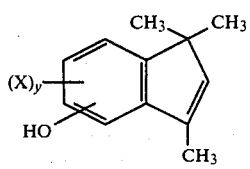

wherein

X represents a hydrogen atom, a halogen atom, a hydroxyl group or a methyl group, and y is 0 or an integer of 1 to 3, which comprises heat-decomposing at least one isopropenyl phenol compound selected from the group consisting of isopropenyl phenol monomers of the formula

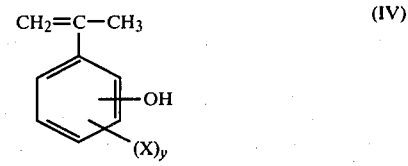

wherein X and y are as defined, oligomers and polymers of isopropenyl phenols expressed by the formula

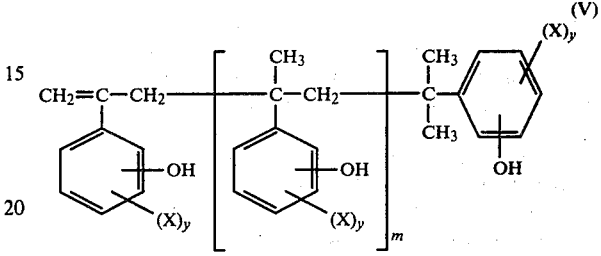

wherein

X and y are as defined, and m is 0 or an integer of up to 10,000, and oligomers and polymers of isopropenyl phenols expressed by the formula

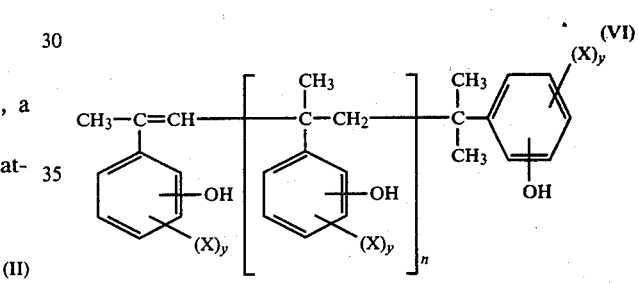

wherein X and y are as defined, and n is 0 or an integer of up to 10,000, in the presence of an acid catalyst.

Alkali-catalyzed heat decomposition of phenolic compounds was previously discussed in Soviet Pat. No. 303,314 and Japanese Laid-Open Patent Publication No. 13341/75 which disclose a process for producing phenol and p-iospropenyl phenol by heat decomposing bisphenol A in the presence of sodium hydroxide at 200° to 260° C. and 10 mmHg or at 180° to 210° C. and 4 mmHg.

Acid-catalyzed heat decomposition of phenolic compounds was previously discussed in The Journal of Organic Chemistry, Vol. 23, p. 549 (1958) which discloses a process comprising heating bisphenol A at 250° C. in the presence of solid phosphoric acid to decompose it into phenol and p-isopropenyl phenol.

No report has been made in the literature, however, about the thermal decomposition reaction of phenolic compound having a tough skeleton such as indane compounds in the presence of an alkali or acid catalyst. Neither is there known a method for producing indene compounds from isopropenyl phenol monomers, isopropenyl phenol oligomers, and/or isopropenyl phenol polymers in the presence of acid catalysts.

Our extensive investigations have now led to the discovery that indene compounds of formula (III) including the novel indene compound of formula (I) can be produced by heat decomposition of phenolic indane compounds in the presence of acid or alkaline catalysts, or by heat decomposition of isopropenyl phenol monomers, isopropenyl phenol oligomers, and/or isopropenyl phenol polymers in the presence of acid catalysts.

The indene compounds produced by this invention are useful as raw materials for novel carbamate and organophosphorus agricultural chemicals and novel indane musk. Polymers of the indene compounds in accordance with this invention are novel phenolic resins, and are useful, for example, as raw materials or modifiers of resol resins or novolak resins. These resins can also find application in the fields of varnish, paint, adhesive, laminate, casting, molding, coating and packaging. Polymerization of the indene compounds in this invention with other vinyl monomers gives novel copolymers which can be used in coatings and adhesives. Moreover, when the indene compounds in accordance with this invention are reacted with drying oils or diene polymers, modified drying oils or diene polymers having a hydroxyindane skeleton can be obtained. Thus, the indene compounds obtained by this invention are commercially useful as raw materials and intermediates for organic syntheses.

According to one embodiment of this invention, indene compounds of formula (III), such as 5-hydroxy-1,1,3-trimethyl-2-indene of formula (I), can be produced by heat decomposing an indane compound of formula (II), such as 5-hydroxy-3-(4-hydroxyphenyl)-1,1,3-trimethylindane, in the presence of an acid or alkaline catalyst.

The indane compound of formula (II) can be produced by heating a compound of formula (IV), (V) and/or (VI) to a suitable temperature to form a linear dimer of the isopropenyl phenol of formula (IV), and intramolecularly cyclizing the linear dimer in the presence of an acid catalyst. The compound of formula (II) can also be produced by heating the compound of formula (IV), (V) and/or (VI) in the presence of an acid catalyst.

Examples of the indane compound of formula (II) include:
4-hydroxy-3-(3-hydroxyphenyl)-1,1,3-trimethylindane,
5-hydroxy-3-(4-hydroxyphenyl)-1,1,3-trimethylindane,
6-hydroxy-3-(3-hydroxypheny)-1,1,3-trimethylindane,
7-hydroxy-3-(2-hydroxyphenyl)-1,1,3-trimethylindane,
5-hydroxy-6-chloro-3-(4-hydroxy-3-chlorophenyl)-1,1,3-trimethylindane,
5-hydroxy-4,6-dichloro-3-(4-hydroxy-3,5-dichlorophenyl)-1,1,3-trimethylindane,
5-hydroxy-6-bromo-3-(4-hydroxy-3-bromophenyl)-1,1,3-trimethylindane,
5-hydroxy-4,6-dibromo-3-(4-hydroxy-3,5-dibromophenyl)-1,1,3-trimethylindane,
5-hydroxy-6-methyl-3-(4-hydroxy-3-methylphenyl)-1,1,3-trimethylindane,
5-hydroxy-4,6-dimethyl-3-(4-hydroxy-3,5-dimethylphenyl)-1,1,3-trimethylindane, and
5,7-dihydroxy-3-(2,4-dihydroxphenyl)-1,1,3-trimethylindane.

Examples of suitable acid catalysts for use in this invention are protonic acids such as sulfuric acid, phosphoric acid, polyphosphoric acid, benzenesulfonic acid, toluenesulfonic acid and methanesulfonic acid, Lewis acids such as aluminum chloride, ferric chloride, stannic chloride and boron fluoride, and solid acids such as activated clay, silica-alumina and ion exchange resins having sulfonic groups. Suitable alkaline catalysts include sodium hydroxide, potassium hydroxide, sodium carbonate, potassium carbonate, sodium phenolate and sodium acetate.

Usually, the heat decomposition reaction is carried out in the presence of a solvent, for example inert high-boiling oils such as mineral oils and synthetic oils, phenol, cresol, diphenyl ether, benzene, toluene, or methylene chloride. The amount of the solvent is not more than 50 times, preferably not more than 10 times, the weight of the indane compound of formula (II). It may, however, be carried out in the absence of solvent. When the heat decomposition is carried out in the presence of an acid catalyst, the amount of the acid catalyst is 0.01 to 20% by weight, preferably 0.1 to 10% by weight, based on the indane compound of formula (II). The reaction is carried out under atmospheric, elevated or reduced pressure, preferably atmospheric pressure to 5 mmHg, a temperature of from 40° to 300° C., preferably from 150° to 280° C. When the heat decomposition is carried out in the presence of an alkaline catalyst, the amount of the alkaline catalyst is 0.01 to 15.0% by weight, preferably 0.1 to 2.0% by weight, based on the indane compound of formula (II). The reaction is carried out usually under a pressure of 200 mmHg to 5 mmHg at a temperature of 180° to 280° C., preferably under a reduced pressure of 10 to 50 mmHg at a temperature of 210° to 250° C.

The reaction time is in the range of 0.1 to 20 hours in the presence of either the acid catalyst or the alkaline catalyst. When the reaction is carried out batchwise, the solvent, the starting indane compound and the catalyst may be fed simultaneously; or the indane compound is first dissolved in the solvent and then the catalyst is added. When the solvent is not added, the starting compound and the catalyst are fed simultaneously, or the starting compound is first melted by heating and then the catalyst is fed. The reaction can of course be carried out by a continuous process.

According to another embodiment of this invention, the indane compound of formula (III) can be produced by heat decomposing at least one isopropenyl phenol compound selected from the group consisting of isopropenyl phenol monomers of formula (IV), oligomers and polymers of isopropenyl phenols expressed by formula (V) and oligomers and polymers of isopropenyl phenols expressed by formula (VI) in the presence of acid catalysts.

Examples of the isopropenyl phenol monomers of formula (IV) are isopropenyl phenol (ortho-, meta-, paraisomers), isopropenyl cresol, isopropenyl catechol, isopropenyl hydroquinone, 3-chloro-4-hydroxy-α-methylstyrene, 3,5-dichloro-4-hydroxy-α-methylstyrene, 3,5-dimethyl-4-hydroxy-α-methylstyrene, and 4-chloro-3-hydroxy-α-methylstyrene.

Examples of the oligomers or polymers of formula (V), especially compounds of formula (V) in which m is zero [i.e., linear dimers of the compounds of formula (IV)] include:
4-methyl-2,4-bis(2-hydroxyphenyl)-pent-1-ene,
4-methyl-2,4-bis(3-hydroxyphenyl)-pent-1-ene,
4-methyl-2,4-bis(4-hydroxyphenyl)-pent-1-ene,
4-methyl-2,4-bis(dihydroxyphenyl)-pent-1-ene,
4-methyl-2,4-bis(cresyl)-pent-1-ene,
4-methyl-2,4-bis(3-chloro-4-hydroxyphenyl)-pent-1-ene,
4-methyl-2,4-bis(3,5-dichloro-4-hydroxyphenyl)-pent-1-ene,
4-methyl-2,4-bis(3,5-dimethyl-4-hydroxyphenyl)-pent-1-ene, 4-methyl-2,4-bis(4-chloro-3-hydroxyphenyl)-pent-1-ene, and
4-methyl-2,4-bis(3-chloro-2-hydroxyphenyl)-pent-1-ene.

Examples of the oligomers or polymers of formula (VI), especially those of formula (VI) in which n is zero (i.e., linear dimers of the compounds of formula (IV), which are isomers of the aforesaid compounds of formula (V) in which m is zero in formula (V)] include:
4-methyl-2,4-bis(2-hydroxyphenyl)-pent-2-ene,
4-methyl-2,4-bis(3-hydroxyphenyl)-pent-2-ene,
4-methyl-2,4-bis(4-hydroxyphenyl)-pent-2-ene,
4-methyl-2,4-bis(dihydroxyphenyl)-pent-2-ene,
4-methyl-2,4-bis(cresyl)-pent-2-ene,
4-methyl-2,4-bis(3-chloro-4-hydroxyphenyl)-pent-2-ene,
4-methyl-2,4-bis(3,5-dichloro-4-hydroxyphenyl)-pent-2-ene,
4-methyl-2,4-bis(3,5-dimethyl-4-hydroxyphenyl)-pent-2-ene,
4-methyl-2,4-bis(4-chloro-3-hydroxyphenyl)-pent-2-ene, and
4-methyl-2,4-bis(3-chloro-2-hydroxyphenyl)-pent-2-ene.

Suitable acid catalysts used in the heat decomposition of the compounds of formula (IV), (V) and/or (VI) include protonic acids such as sulfuric acid, phosphoric acid, polyphosphoric acid, benzenesulfonic acid, toluenesulfonic acid and methanesulfonic acid, Lewis acids such as aluminum chloride, ferric chloride, stannic chloride and boron fluoride, and solid acids such as activated clay, silica-alumina and ion exchange resins having sulfonic groups. These catalyst compounds may be used in combination with each other, as required.

The heat decomposition reaction is carried out usually in the presence of a solvent, for example aromatic compounds such as benzene, toluene, xylene, chlorobenzene and anisole, halogenated hydrocarbons such as methylene chloride, carbon tetrachloride, chloroform and ethylene dichloride, and high-boiling ethers such as diphenyl ether. The amount of the solvent is not more than 50 times, preferably not more than 10 times, the weight of the compound of formula (IV), (V) and/or (VI). These solvents may be used in combination with each other, as required. Or such solvents may be used in combination with alcohols, ketones or esters. Of course, the heat decomposition reaction may be performed in the absence of solvent.

The acid catalyst is used in an amount of 0.01 to 20% by weight, preferably 1 to 10% by weight, based on the total weight of the compound of formula (IV), (V) and/or (VI). The reaction can be carried out at atmospheric, elevated or reduced pressure, preferably atmospheric pressure to a reduced pressure of 5 mmHg, at a temperature of 40° to 300° C.

In performing the above process, there may be used a two-step procedure which comprises first heating the compound of formula (IV), (V) and/or (VI) at 40° to 150° C. to form the indane compound of formula (II), and then heating the indane compound at 180° to 300° C. to form the indene compound of formula (III). Or the indene compound of formula (III) may be produced by heating the starting compound at 150° to 250° C. in one step using a high-boiling solvent. Still another procedure may be employed which comprises heating the starting compound at 40° to 150° C. to form the indane compound of formula (II), then adding the alkaline catalyst, and reacting the indane compound to form the indene compound of formula (III).

The reaction time required in the above process is from 0.1 to 24 hours. When the reaction is carried out batchwise, the acid catalyst may be fed simultaneously with the charging of the solvent and starting compound or after dissolving the starting compound in the solvent. When the reaction is carried out in the absence of a solvent, the starting compound and the catalyst are fed simultaneously; or the catalyst is fed after heat-melting the starting compound. Of course, the reaction may be carried out by a continuous process.

The following Examples illustrate the present invention more specifically.

The accompanying drawing (FIG. 1) is an infrared absorption spectral chart of 5-hydroxy-1,1,3-trimethyl-2-indene obtained in Example 1.

EXAMPLE 1

A 500 ml separable flask equipped with a thermometer, an agitator and a distillation column (2.5 cm in inside diameter, 10 cm in length, filled with glass beads having a diameter of 8 mm) was charged with 300.0 g of 5-hydroxy-3-(4-hydroxyphenyl)-1,1,3-trimethylindane, 60.0 g of phenol as a solvent and 3.0 g of granular sodium hydroxide. The temperature of the inside of the flask was raised, and when the starting material was completely dissolved at 180° C., agitation of the mixture was started. When the inside temperature reached 200° C., the pressure of the inside of the flask was reduced to 50 mmHg, at which time distillation began. Subsequently, the temperature of the inside of the flask was raised to 250° C., and simultaneously, the pressure was reduced to 10 mmHg. Distillation was continued under these conditions. In about 2 hours, the distillation was over and 342.3 g of a distillate was obtained.

The distillate was distilled in a distillation column (2.5 cm in inside diameter, 30 cm in length, filled with glass beads having a diameter of 8 mm) to afford 159.8 g of phenol and 164.0 g (yield 84.2%) of a fraction (145°–147° C./15 mmHg) having a melting point of 131° to 132° C. This fraction was determined to be 5-hydroxy-1,1,3-trimethyl-2-indene by infrared absorption spectroscopy (IR), nuclear magnetic resonance spectroscopy (NMR), mass analysis (Mass) and elemental analysis. The properties of this product are shown below.

Melting point: 131°–132° C.
Boiling point: 145°–147° C./15 mmHg
IR spectrum (KBr method): shown in FIG. 1.
NMR (acetone-$d_6$; internal reference TMS; 60 MHz):

δ (ppm)

1.23 (methyl group at the 1-position)
2.00 (methyl group at the 3-position)
5.98 (proton at the 2-position)
6.5–7.2 (proton of the benzene ring)
7.93 (proton of the —OH group)
Mass: M+ m/e 174

| Elemental analysis: For $C_{12}H_{14}O$ | | |
| --- | --- | --- |
|  | C % | H % |
| Calculated: | 82.72 | 8.10 |
| Found: | 82.80 | 8.12 |

EXAMPLE 2

The same reaction flask as in Example 1 was chared with 300.0 g of 5-hydroxy-3-(4-hydroxyphenyl)-1,1,3-trimethylindane and 100 g of a high-boiling oil (Nuray-N180, a trademark for a product of Esso Standard Oil Co.) as a solvent, and the temperature of the inside of the flask was raised. After the stirring compound was completely dissolved at 210° C., agitation of the mixture was started. Then, 2.6 g of solid anhydrous sodium carbonate was added. When, after a lapse of 30 minutes, the pressure was reduced to 50 mmHg, distillation began. Subsequently, the temperature of the inside of the flask was gradually raised to 250° C., and simultaneously, the pressure was reduced to 10 mmHg. In about 1.5 hours, the distillation was over and 274.7 g of a distillate was obtained. Gas-chromatographic analysis of the distillate showed that 105.2 g of phenol and 169.5 g (yield 87.0%) of 5-hydroxy-1,1,3-trimethyl-2-indene were formed.

EXAMPLE 3

The same separable flask as in Example 1 except having a capacity of 1,000 ml was charged with 600 g of 5-hydroxy-3-(4-hydroxyphenyl)-1,1,3-trimethylindane and 100 g of phenol as a solvent, and the temperature of the inside of the flask was raised. After the starting compound was completely dissolved at 180° C., 35 g of a 20% aqueous solution of sulfuric acid was added. The water that distilled was completely removed. When the temperature of the inside of the flask was maintained at 180° to 200° C. and the pressure was reduced to 50 mmHg, distillation began. Subsequently, the pressure was slowly reduced to 10 mmHg and the inside temperature was elevated slowly to 230° C. In about 5 hours, the distillation was over and 590 g of a distillate was obtained. Gas-chromatographic analysis of the distillate showed that 280 g of phenol and 310 g (yield 81.6%) of 5-hydroxy-1,1,3-trimethyl-2-indene were formed.

EXAMPLE 4

The same separable flask as in Example 1 except having a capacity of 300 ml was charged with 200 g of an isopropenyl phenol mixture consisting of 2.5% by weight of p-isopropenyl phenol monomer, 72% by weight of a linear dimer of p-isopropenyl phenol, 4.3% by weight of a linear trimer of p-isopropenyl phenol, 2.1% by weight of a linear tetramer of p-isopropenyl phenol, 0.9% by weight of a linear pentamer, 1.5% by weight of a linear hexamer and higher polymers and 16.7% by weight of other phenolic compounds, and the temperature of the inside was raised. When the contents were completely melted, 10 g of a 10% aqueous solution of sulfuric acid was added. With stirring, the pressure was slowly reduced to 10 mmHg. Distillation began at 130° C. The temperature of the inside was raised to 180° C., and the reaction was performed for 4 hours while allowing distillation. Subsequently, the inside temperature was slowly raised from 180° C. to 260° C. while continuing distillation. In about 6 hours, the distillation was over, and 158 g of a distillate was obtained. Gas-chromatographic analysis of the distillate showed that 55.4 g of phenol and 102.6 g (yield 94.8%) of 5-hydroxy-1,1,3-trimethyl-2-indene were formed.

EXAMPLE 5

The same reaction flask as in Example 3 was charged with 300 g of the same mixture of isopropenyl phenol compounds as used in Example 4, 500 g of benzene and 15 g of a 10% aqueous solution of sulfuric acid, and with stirring at 80° C., the reaction was performed for 4 hours. Then, 9.0 g of a 40% aqueous solution of sodium hydroxide was added, and the benzene was distilled off. Subsequently, the temperature was raised. When the inside temperature reached 180° C. and the contents of the flask were dissolved completely, the pressure was reduced while stirring the solution. Distillation began at an inside temperature of 200° C. under a pressure of 50 mmHg. The inside temperature was then raised to 260° C., and simultaneously, the pressure was reduced to 10 mmHg. In about 2.5 hours, the distillation was over, and 225 g of a distillate was obtained. Gas-chromatographic analysis of the distillate showed that 78.9 g of phenol and 146.1 g (yield 90.0%) of 5-hydroxyl-1,1,3-trimethyl-2-indene were formed.

What we claim is:

1. A process for producing an indene compound of the formula

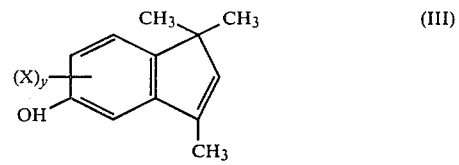

wherein X represents a hydrogen atom, a halogen atom, a hydroxyl group, or a methyl group, and y is 0 or an integer of from 1 to 3, which comprises heat-decomposing an indane compound of the formula

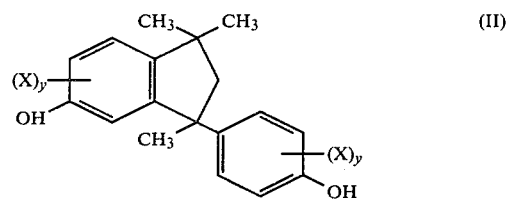

wherein X and y are as defined, in the presence of an acid or alkaline catalyst.

2. A process as claimed in claim 1 wherein said catalyst is present in an amount of 0.01 to 20% by weight of said indane compound and said heat decomposition is at a temperature of from 40° C. to 300° C.

3. A process as claimed in claim 2 wherein said catalyst is an acidic catalyst.

4. A process as claimed in claim 6 wherein said temperature is from 150° C. to 280° C.

5. A process as claimed in claim 4 wherein the amount of catalyst is 0.1 to 10% by weight of said indane compound and said heat decomposition is carried out at a pressure of from atmospheric to 5 mmHg.

6. A process as claimed in claim 3 wherein said acid catalyst is selected from the group consisting of sulfuric acid, phosphoric acid, polyphosphoric acid, benzenesulfonic acid, toluenesulfonic acid, methanesulfonic acid, aluminum chloride, ferric chloride, stannic chloride, boron fluoride, activated clay, silica-alumina and ion exchange resins having sulfonic groups.

7. A process as claimed in claim 1 wherein said heat decomposition is in the presence of 0.01 to 20% by weight of an acidic catalyst at a temperature of 40° to 300° C. or in the presence of 0.01 to 15.0% by weight of an alkaline catalyst at a temperature of from 180° C. to 280° C., said weight percentages being based upon the weight of said indane compound.

8. A process as claimed in claim 7 wherein the catalyst is an alkaline catalyst and the decomposition is carried out at a pressure of 200 mmHg to 5 mmHg.

9. A process as claimed in claim 8 wherein the temperature is 210° to 250° C. and the pressure is 10 to 50 mmHg.

10. A process as claimed in claim 8 wherein the alkaline catalyst is selected from the group consisting of sodium hydroxide, potassium hydroxide, sodium carbonate, potassium carbonate, sodium phenolate and sodium acetate.

11. A process as claimed in claim 7 wherein the heat decomposition is carried out in the presence of a solvent selected from the group consisting of inert high-boiling oils, phenol, cresol, diphenyl ether, benzene, toluene, and methylene chloride.

12. A process as claimed in claim 7 wherein the catalyst is an acidic catalyst and said decomposition is carried out at a pressure of from 5 mmHg to atmospheric pressure.

* * * * *